United States Patent
Hill et al.

(10) Patent No.: US 11,122,999 B2
(45) Date of Patent: Sep. 21, 2021

(54) OPTOKINESYS

(71) Applicant: Cornell University, Ithaca, NY (US)

(72) Inventors: Nicholas Jeremy Hill, White Plains, NY (US); Glen T. Prusky, White Plains, NY (US); Jason B. Carmel, Mamaroneck, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 265 days.

(21) Appl. No.: 16/314,124

(22) PCT Filed: Jun. 30, 2017

(86) PCT No.: PCT/US2017/040366
§ 371 (c)(1),
(2) Date: Dec. 28, 2018

(87) PCT Pub. No.: WO2018/006013
PCT Pub. Date: Jan. 4, 2018

(65) Prior Publication Data
US 2019/0320962 A1    Oct. 24, 2019

Related U.S. Application Data

(60) Provisional application No. 62/357,122, filed on Jun. 30, 2016.

(51) Int. Cl.
*A61B 5/16* (2006.01)
*A61B 3/113* (2006.01)
*A61B 5/00* (2006.01)

(52) U.S. Cl.
CPC .............. *A61B 5/163* (2017.08); *A61B 3/113* (2013.01); *A61B 5/0077* (2013.01); *A61B 5/486* (2013.01);

(Continued)

(58) Field of Classification Search
CPC ..... A61B 3/0025; A61B 3/0041; A61B 3/005; A61B 3/0058; A61B 3/0091; A61B 3/02;
(Continued)

(56) References Cited

U.S. PATENT DOCUMENTS 10,362,934 B2 * 7/2019 Greivenkamp, Jr. ........................ A61B 3/0025
2006/0270945 A1    11/2006 Ghajar
(Continued)

FOREIGN PATENT DOCUMENTS

WO    WO-2015003097 A1 *    1/2015    ............. A61B 3/112

OTHER PUBLICATIONS

Pieh, et al. "Smooth pursuit in infants: maturation and the influence of stimulation." British journal of ophthalmology 96.1 (2012): 73-77. (Year: 2012).*

(Continued)

*Primary Examiner* — David J. McCrosky
(74) *Attorney, Agent, or Firm* — Foley & Lardner LLP

(57) ABSTRACT

The present system can measure eye gaze position and detect, in near real-time, smooth eye movements that are driven by a moving stimulus. Smooth movements that match the velocity of a moving stimulus provide evidence that the subject can see the moving stimulus. The present system can give real-time feedback to the user, for example in the form of music, contingent on the ability of the user to perform smooth velocity-matched eye movements. The present system can measure visual impairment and train visual ability both for rehabilitation and development purposes.

18 Claims, 6 Drawing Sheets

(52) U.S. Cl.
    CPC ............ *A61B 5/7405* (2013.01); *A61B 5/746* (2013.01); *A61B 5/4088* (2013.01)

(58) Field of Classification Search
    CPC ........... A61B 3/11; A61B 3/112; A61B 3/113; A61B 3/145; A61B 5/162; A61B 5/163; A61B 5/165; A61B 5/168; A61B 5/4064; A61B 5/4082; A61B 5/4088; A61B 5/4842
    See application file for complete search history.

(56) References Cited

U.S. PATENT DOCUMENTS

2014/0320817 A1   10/2014  Kiderman et al.
2014/0356842 A1   12/2014  Duffy

OTHER PUBLICATIONS

Von Hofsten, et al. "Development of smooth pursuit tracking in young infants." Vision research 37.13 (1997): 1799-1810. (Year: 1997).*

International Search Report and Written Opinion, PCT/US2017/040366, Cornell University, 6 pages dated Sep. 15, 2017.

\* cited by examiner

OPTOKINESYS

CROSS-REFERENCE TO RELATED APPLICATION

This application is a National Stage Application of PCT/US2017/040366, filed Jun. 30, 2017, which claims the benefit of priority to U.S. Provisional Patent Application 62/357,122, filed Jun. 30, 2016, which is hereby incorporated by reference in its entirety.

BACKGROUND OF THE DISCLOSURE

The human eye moves in distinct ways, depending on the circumstances. One type of movement is a smooth movement that occurs when the eye is tracking an object that is also moving smooth across the subject's visual field. The object provides the subject with a target on which the subject focuses as the object moves across the visual field. A second type of movement is free scanning. During this type of movement, the subject scans by making sudden transitions between multiple fixation points. Without a moving object to track, a user cannot generate smooth eye movements.

SUMMARY OF THE DISCLOSURE

The present system can measure eye gaze position and detect, in near real-time, smooth eye movements that are driven by a moving stimulus. Smooth movements that match the velocity of a moving stimulus provide evidence that the subject can see the moving stimulus. The present system can measure visual impairment and train visual ability both for rehabilitation and development purposes. For example, the system can alter the contrast and spatial frequency of the stimulus to determine the limits of the subject's visual ability. Because the smooth movements are difficult to fabricate when a stimulus cannot be seen, and the system can monitor the movements without verbal responses from the subject, the system can be used to test the visual ability of a subject with neurological impairments that might prevent the subject from communicating. The system can also be implemented into rehabilitation systems and interactive toys to train infants and reinforce the development of visual processing and visuomotor coordination.

According to one aspect of the disclosure, a system to detect smooth eye movements includes a display. The system can include an eye-tracking monitor. The eye-tracking monitor can be configured to detect a gaze position of an eye. The system can include a pursuit detector that is executed by at least one processor of a data processing system. The pursuit detector is configured to display a visual stimulus that moves from a first location on the display to a second location on the display. The pursuit detector is also configured to simultaneously receive, from the eye-tracking monitor, a gaze position signal detected as the visual stimulus moves from the first location to the second location. The pursuit detector can calculate a smooth-movement score vector from the gaze position signal. The smooth-movement score vector can indicate a movement relationship level between the gaze position signal and the visual stimulus moving from the first location to the second location. The pursuit detector can trigger, responsive to the smooth-movement score vector being above a predetermined threshold, a notification. The notification can provide discrete or continuous feedback.

The gaze position signal can be a gaze position signal that indicates a horizontal gaze position of the eye. The pursuit detector can be configured to compute a velocity vector from the gaze position signal and determine a stimulus-correlated gaze velocity estimate based on velocity vector and the speed at which the visual stimulus moves from the first location to the second location. The pursuit detector 106 can calculate the smooth-movement score vector based on the stimulus-correlated gaze velocity estimate.

The gaze position signal can include a plurality of samples, and the pursuit detector can be configured to generate a count of the plurality of samples in each of a plurality of predetermined target velocity ranges. The pursuit detector can calculate the smooth-movement score vector based on the count of the plurality of samples in each of the predetermined target velocity ranges.

The pursuit detector can be configured to change a spatial frequency of the visual stimulus. The pursuit detector can be configured to change a contrast of the visual stimulus. The notification can include an audible notification, such as music, tactile notifications that provide tactile feedback, or visual notifications that provide colored light feedback.

The pursuit detector can be configured to display a second visual stimulus from the first location to the second location. The second visual stimulus can have a spatial frequency or a contrast different than the visual stimulus.

The display can include a motor. The pursuit detector can drive the motor at a predetermined speed to move the visual stimulus from the first location to the second location. The visual stimulus can be a physical visual stimulus.

According to an aspect of the disclosure, a method includes displaying, on a display, a visual stimulus moving from a first a location to a second location. The method can include generating, by an eye-tracking monitor, a gaze position signal as the visual stimulus moves from the first location to the second location. The gaze position signal can indicate the position of an eye. The method can include calculating a smooth-movement score vector from the gaze position signal. The smooth-movement score vector can indicate a movement relationship level between the gaze position signal and the visual stimulus moving from the first location to the second location. The method can include triggering, responsive to the smooth-movement score vector being above a predetermined threshold, a notification.

In some implementations, the gaze position signal is a horizontal gaze position signal indicating a horizontal gaze position of the eye. The method can include computing a velocity vector from the gaze position signal. The method can include determining a stimulus-correlated gaze velocity estimate based on velocity vector and speed of the visual stimulus as the visual stimulus moves from the first location to the second location. The method can include calculating the smooth-movement score vector based on the stimulus-correlated gaze velocity estimate.

The method can include generating, from the gaze position signal, which can include a plurality of samples, a count of the plurality of samples in each of a predetermined target velocity range. The method can include calculating the smooth-movement score vector based on the count of the plurality of samples in each of the predetermined target velocity ranges.

The method can include changing a spatial frequency of the visual stimulus. The method can include changing a contrast of the visual stimulus. The method can include generating an audible notification.

The method can include displaying a second visual stimulus from the first location to the second location. The second visual stimulus can have a spatial frequency or a contrast different than the visual stimulus. The method can include driving a motor of the display at a predetermined speed to move the visual stimulus from the first location to the second location. The visual stimulus can be a physical visual stimulus.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings.

DETAILED DESCRIPTION

Following below are more detailed descriptions of various concepts related to, and implementations of, methods, apparatuses, and systems to eye tracking and diagnostics. The various concepts introduced above and discussed in greater detail below may be implemented in any of numerous ways.

Figure 1:
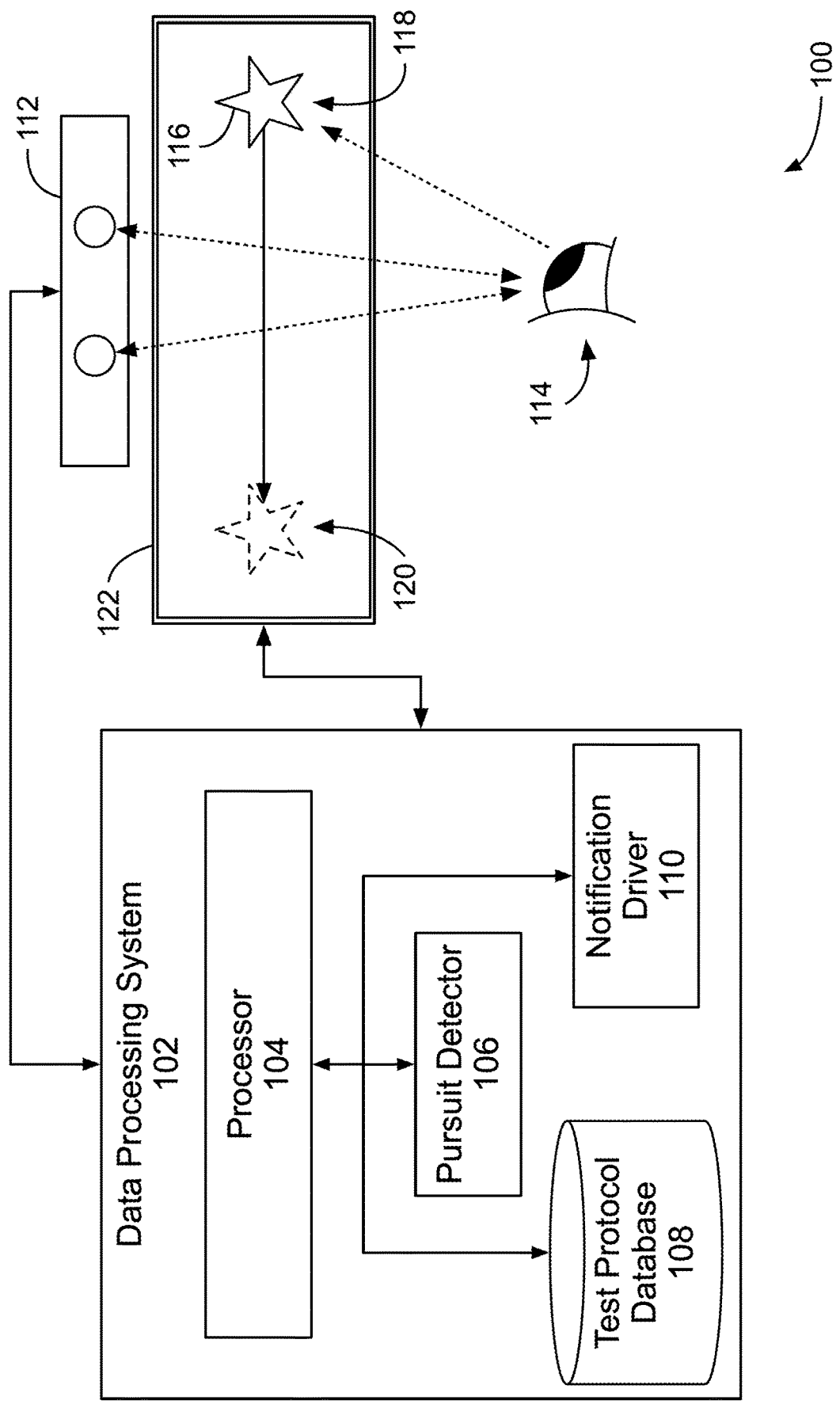
FIG. 1 illustrates a block diagram of an example system for detecting smooth eye movements.

FIG. 1 illustrates a block diagram of an example system 100 for detecting smooth eye movements. The system 100 includes a data processing system 102 that measures the eye movements of a subject or patient and detects smooth eye movements with the measured eye movements. The data processing system 102 can include a processor 104 that can execute a pursuit detector 106. The data processing system 102 can include a test protocol database 108 and a notification driver 110. The data processing system 102 can include or can be coupled with an eye-tracking monitor 112. The eye-tracking monitor 112 can measure the gaze position of a subject's eye 114 as the subject watches a visual stimulus 116 move from a first location 118 to a second location 120 on a display 122.

As an overview, the pursuit detector 106 can be any script, file, program, application, set of instructions, or computer-executable code, that is configured to enable the data processing system 102 to detect smooth eye movements. The pursuit detector 106 can generate images that are displayed to a subject via the display 122. The images can include visual stimuli 116 that move across the display 122. The pursuit detector 106 can move the visual stimulus 116 from a first location 118 to a second location 120. In moving from the first location 118 to the second location 120, the pursuit detector 106 can scroll the image that includes the visual stimulus 116. The pursuit detector 106 can scroll the image in a looping scroll such that once a portion of the image scrolls off an edge of the display 122, the portion can reappear on the opposite edge of the display. The visual stimulus 116 can move from the first location 118 to the second location 120 in a linear or non-linear fashion. The visual stimulus 116 can move along a trajectory that includes horizontal movements, vertical movements, circular movements, movements that change direction, smooth movements, irregular movements, or any combination thereof. The movement from the visual stimulus 116 from the first location 118 to the second location 120 can be at a constant or varying speed.

The pursuit detector 106 can receive from the eye-tracking monitor 112, a gaze position signal. The gaze position signal can include a plurality of samples that each indicate the gaze position of the eye 114 at a given point in time. As described below further, the pursuit detector 106 can generate a smooth-movement score vector that indicates a relationship between the subject's gaze position and the movement of the visual stimulus 116. The smooth-movement score vector can indicate a strength of the correlation between the subject's gaze position and the movement of the visual stimulus 116. The smooth-movement score vector can be a measure of the smoothness of the eye movement over time. The smooth-movement score vector can provide an indication of whether the subject is watching (or can detect) the visual stimulus 116 move across the display 122. If the pursuit detector 106 determines the smooth-movement score vector is above a predetermined threshold, the pursuit detector 106 can trigger the notification driver 110 to provide a notification to the user or caretaker. The notification can continue while the smooth-movement score vector remains above the predetermined threshold.

Referring to FIG. 1, and in greater detail, the system 100 can include an eye-tracking monitor 112. The eye-tracking monitor 112 can include one or more cameras that can capture sequential images of the eye 114. The cameras can capture images of the eye 114 as the eye-tracking monitor 112 projects near-infrared light onto the eye 114. The eye-tracking monitor 112 compares the neighboring images in the captured sequential images to determine the eye's position and gaze point. The eye-tracking monitor 112 can generate a gaze position signal that includes the gaze point as measured at each of the sequential images. In some implementations, some or all of the processing of the gaze position detection can be performed by the data processing system 102. One example eye-tracking monitor 112 is the Tobii Rex Tracker (made available by Tobii of Stockholm, Sweden). The eye-tracking monitor 112 can be a non-near-infrared light based system.

The display 122 can be a computer monitor or other type of display. For example, the display 122 can be the screen of a tablet computer, a computer, smartphone, or virtual reality goggles. The pursuit detector 106 can generate the images that are rendered onto the display 122. The images can include the visual stimulus 116. The visual stimulus 116 can be a specific object, as illustrated in FIG. 1, that can scroll from a first position 118 to a second position 120 on the display 122. The visual stimulus 116 can be the image itself. For example, the image can be a scene that includes a plurality of objects (e.g., a cityscape with buildings, landscape with trees, scene with cartoon or other characters) that move across the display 122. The visual stimulus 116 can be a patterned image. For example, the pattern can include a plurality of shapes and lines. The visual stimulus 116 can be any object or image that is scrolled across the display 122. The visual stimulus 116 can include a plurality of objects.

The plurality of object can be different images. The plurality of objects can scroll or otherwise move independent of one another. For example, the objects can scroll at different speeds.

In some implementations, the system 100 can prevent one of the eyes 114 from seeing the display 122 to assess or train one eye 114 at a time. With virtual reality goggles, the system can blank out half of the stereo display. In desktop setups, the subject can wear 3D cinema glasses and a circular-polarizing sheet is placed over the display 122. The polarizing sheet prevents light from the display 122 from passing through one of the two polarizers in the glasses.

In some implementations, the display 122 can be a physical space that includes one or more physical visual stimuli 116. The display 122 can include a motor that drives the visual stimulus 116 across the display 122. The visual stimuli 116 can be, for example, toys, physical objects, or lights. The pursuit detector 106 can control the motor to drive the physical visual stimuli 116 across the display 122.

The data processing system 102 can include a notification driver 110. The pursuit detector 106 can activate the notification driver 110 when the pursuit detector 106 determines the smooth-movement score vector is above a predetermined threshold or when the pursuit detector 106 detects smooth eye movements. The notification driver 110 can be an audio driver that drives a speaker. For example, the data processing system 102 can play music as a notification when smooth eye movements are detected. The notification driver 110 can be a visual driver that activates visual notifications based on the smoothness detection. For example, the notification driver 110 can activate a green light when the pursuit detector 106 detects smooth movements and a red light when the pursuit detector 106 does not detect smooth movements.

The data processing system 102 can include a test protocol database 108. The test protocol database 108 can store a plurality of test protocols. The test protocols can be designed to test the visual acuity or ability of the subject. The test protocols can set the speed at which the visual stimulus 116 scrolls across the display 122. The test protocols can set the spatial frequency and contrast for the visual stimulus 116 for each trial of a test. In one example, the test protocol can set the spatial frequency and contrast to a range that the subject can track smoothly with their eyes. With each subsequent test, the test protocol can instruct the pursuit detector 106 to change the contrast or the spatial frequency of the visual stimulus 116, for example, decreasing the visual stimulus 116 until the subject cannot track the visual stimulus 116. In some implementations, the test protocol can call for the pursuit detector 106 to change the visual stimulus's contrast, spatial frequency, speed, direction, or any combination thereof during a test.

As described above, the pursuit detector 106 can detect the smooth movement of the eye 114. In some implementations, the detection of smooth movements occurs when the eye 114 is visually tracking an object, such as the visual stimulus 116. When not tracking an object, the eye 114 is "free scanning." The free scanning behavior does not have the same level of smoothness as a tracking movement as the eye 114 makes sudden saccadic movements between multiple, short periods of fixation. When not following a visual stimulus 116, the subject cannot generate the same level of smoothness as during the pursuit of a visual stimulus 116.

The pursuit detector 106 can quantify, from moment to moment, the extent to which the gaze position signal from the eye-tracking monitor 112 indicates that the eye 114 is moving smoothly at a predicted velocity. The pursuit detector 106 can indicate the eye 114 is moving smoothly even when the smooth movements are interspersed with saccades as the eye reverts back from the second position 120 (as the visual stimulus 116 scrolls off the display 122) the first position 118 to track a new visual stimulus 116.

The pursuit detector 106 can generate the smooth-movement score vector in near real-time or during offline analysis. During a near real-time analysis mode, the pursuit detector 106 can analyze the most recent 1 to 2 seconds of the signal generated by the eye-tracking monitor 112. The pursuit detector 106 can continually update the smooth-movement score vector by sliding an analysis window in small steps and performing the calculations on the new window. In an offline mode, the pursuit detector 106 can analyze the whole batch of data (or portions thereof) after a measurement session is finished.

The pursuit detector 106 can detect smooth eye movements by analyzing the gaze position signal generated by the eye-tracking monitor 112. The gaze position signal can include samples that represent the horizontal gaze position, vertical gaze position, and a validity indicator. The validity indicator can be a confidence level in the accuracy of the horizontal and vertical gaze position samples at the time sample. The gaze position signal can include a weighted sum or an average of the subject's two eyes 114 or the pursuit detector 106 can receive a gaze position signal for each eye 114.

The pursuit detector 106 can detect smooth eye movements by computing a velocity vector from the gaze position signal. The velocity vector can be calculated as the position of the eye 114 in the current sample [n] minus the gaze position in the most recent, previous sample [n−1]. Comparing neighboring samples can make the calculations of the pursuit detector 106 less subject to a common type of eye-tracker miscalibration that causes systematic positional bias in estimated gaze position—any such bias disappears in the subtraction.

The pursuit detector 106 can project the velocity vector onto the movement vector along which the visual stimulus 116 is (or was) moving. The projection of the velocity vector onto the movement vector generates a stimulus-correlated gaze velocity estimate (SCGVE). The SCGVE can include the sign (+ if moving with the visual stimulus 116 motion and − if against) and relative speed. A relative speed of 1.0 can indicate the velocity exactly matches visual stimulus 116 velocity.

The pursuit detector 106 can smooth the SCGVE with respect to time. The pursuit detector 106 can use a convex weighted moving average, weights being determined by a negative-exponential function of sample age. This can enable the pursuit detector 106 to cope with the variability in the number of samples per second. Other smoothing filters or techniques can be used, such as Kalman filtering.

The pursuit detector 106 can, at pre-defined intervals, perform an evaluation of the SCGVE. The pre-defined intervals can be, for example, every 0.25 seconds, 0.5 seconds, 0.75 seconds, or every second. An evaluation starts by considering smoothed velocity estimates obtained within the last n seconds (n can be, for example, 0.5, 1, 1.5, or 2 seconds). The pursuit detector 106 can count the number of valid samples within the window, as a fraction of the maximum that the eye-tracking monitor 112 can deliver (e.g., the sampling frequency of the eye-tracking monitor 112). The pursuit detector 106 can issue a warning if the number is less than a certain threshold (e.g., less than 50%). The warning can indicate that the subject is not facing the eye-tracking monitor 112 or that the eye-tracking monitor 112 cannot detect eye movement.

The pursuit detector 106 can continue the evaluation by counting the number of valid smoothed velocity samples that fell within a pre-defined target velocity range [$v_{min}$, $v_{max}$] within the last n seconds. The range can include +1.0 and exclude 0.0—for example the range [+0.75, +1.5]. $C_{pos}$ can denote the count of samples that fall within this range. The pursuit detector 106 can also count the number of samples that fall within the negative of this range [$-v_{mass}$, $-v_{min}$] (e.g., within the range [−1.5, −0.75] in this example) and call this count $C_{neg}$. Furthermore, the pursuit detector 106 can count the number $C_{low}$ of samples that fall within the low-velocity range [$-v_{min}/k$, $+v_{min}/k$], and the number $C_{high}$ of samples whose velocity is outside the range [$-k\ v_{max}$, $+k\ v_{max}$]. In some implementations, 1.5 is an appropriate value for the constant k that determines the separation of these velocity ranges.

When $C_{pos}$ is greater than $C_{neg}$, the pursuit detector 106 can perform a binomial test of the null hypothesis that a sample has equal probability (e.g., 0.5) of contributing to either count ($C_{pos}$ or $C_{neg}$). The test can be a one-sided test, such the pursuit detector 106 obtains a p-value close to 0 when $C_{pos} \gg C_{neg}$, and close to 1 when $C_{pos} \ll C_{neg}$. The pursuit detector 106 can obtain the negative log of the test's significance probability, −log(p). The pursuit detector 106 can repeat this test but compare $C_{pos}$ against $C_{low}$ instead of $C_{neg}$. The pursuit detector 106 can repeat it again to compare $C_{pos}$ against $C_{high}$. The smooth movement score is the smallest of the three −log(p) values obtained from the three tests. If $C_{neg} > C_{pos}$, the procedure is the same except that the roles of $C_{neg}$ and $C_{pos}$ should be reversed, and the final score should be multiplied by −1. The result is a directional smooth-movement score. A high positive value indicates strong evidence of smooth eye movements in the direction of the stimulus. A high negative value can indicate smooth eye movement in the wrong direction (opposite to stimulus motion). A small value can indicate other forms of eye movement, but may not rule out smooth movement if this is occurring perpendicular to the direction of stimulus motion or at entirely the wrong speed, but it is likely to indicate more common forms of eye movement such as fixation, or saccades back and forth.

The pursuit detector 106 can output the directional score. In some implementations, the score may be compared to a threshold (e.g., smooth eye movement might be considered to be detected when the score exceeds a certain positive value, such as +1.5, and not detected otherwise). In some implementations, the pursuit detector 106 can increase the threshold based on the level of smoothing the pursuit detector 106 applies to the SCGVE.

Figure 2:
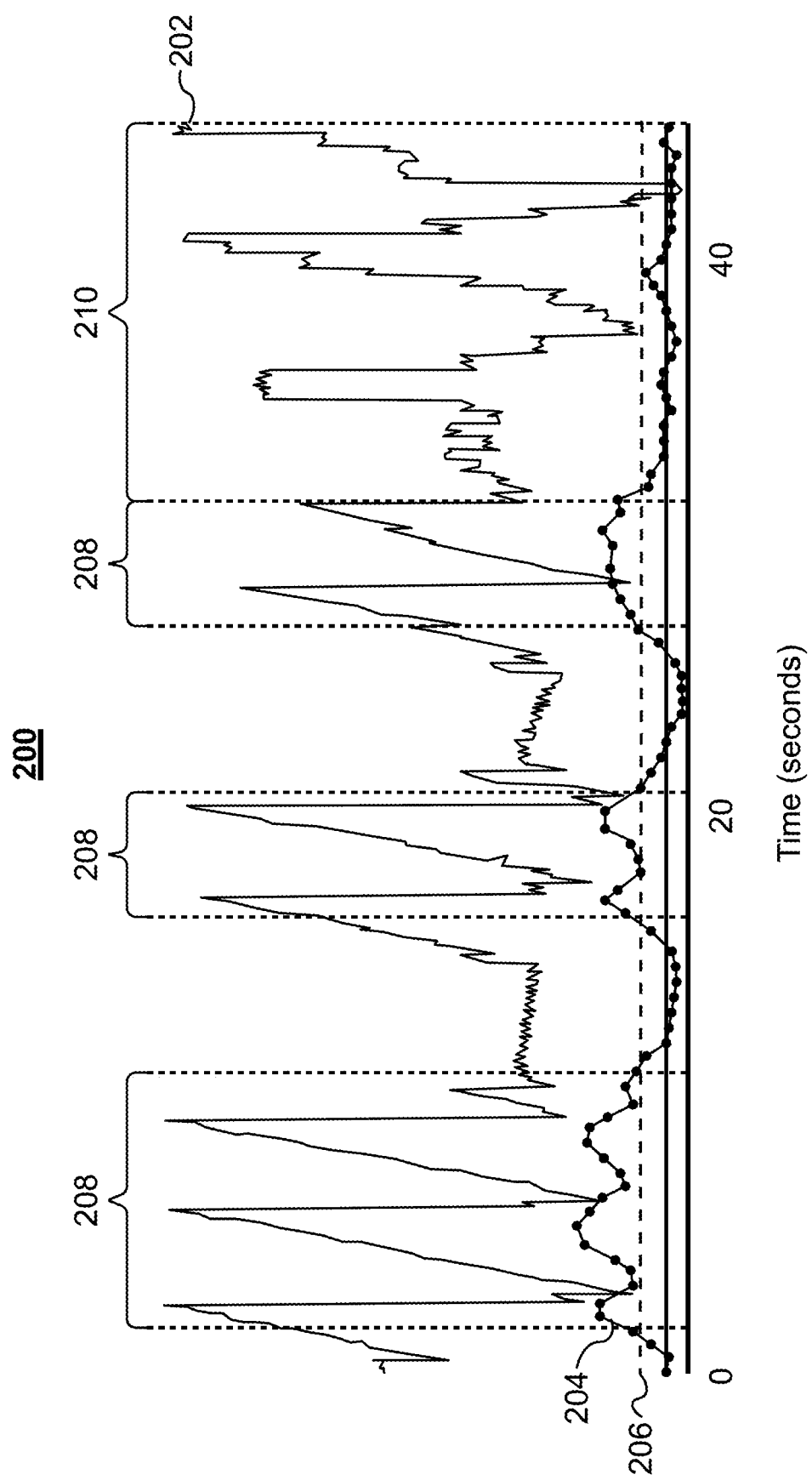
FIG. 2 illustrates an example output plot from the system illustrated in FIG. 1.

FIG. 2 illustrates an example output graph 200 of the system illustrated in FIG. 1. The graph 200 includes a plot 202 of the horizontal gaze position. The graph 200 also includes a plot 204 of the output from the pursuit detector 106 (e.g., the smooth-movement score vector). The graph also illustrates a predetermined threshold. During the time intervals 208, the subject was visually pursuing a visual stimulus 116. As illustrated during the time interval 208, the smooth-movement score vector 204 is above the threshold 206. Accordingly, during these times the pursuit detector 106 indicates that the eye is engaged in smooth movements. As illustrated in the graph 200, when the subject was not pursuing a visual stimulus 116, the smooth-movement score vector 204 is below the predetermined threshold. During the time interval 210, the subject attempted to fake smooth eye movements. However, without tracking a visual stimulus 116, smooth eye movements are difficult to generate, and the pursuit detector 106 correctly determined the subject was not tracking a visual stimulus 116 and not engaged in smooth eye movements.

Figure 3:
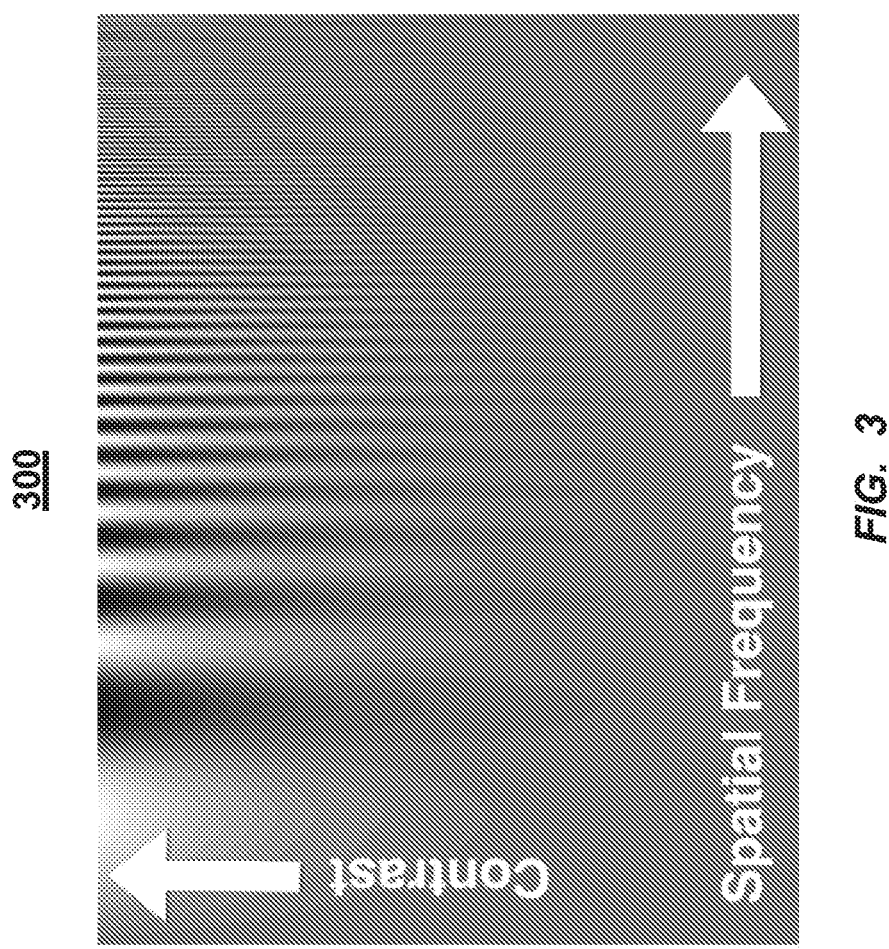
FIG. 3 illustrates a plot of example contrast and spatial frequency settings.

FIG. 3 illustrates a plot 300 of example contrast and spatial frequency settings. As discussed above, the test protocol database 108 can include different test protocols that the pursuit detector 106 can follow to determine or test the visual acuity of the subject. During the tests, the protocols can call for the pursuit detector 106 to alter one or more of the contrast, the spatial frequency, speed, or direction of the visual stimulus 116. The spatial frequency and contrast can be adjusted to ranges that are beyond the visual capability of the subject. Under these conditions, the subject cannot see the visual stimulus 116 well enough to generate smooth eye movements. As the pursuit detector 106 adjusts the spatial frequency and contrast, the pursuit detector 106 can determine the boundary of the subject's visual acuity when the pursuit detector 106 detects the transition between smooth and non-smooth eye movements. In some implementations, the system 100 can include a light sensor that can set the contrast responsive to the ambient lighting conditions.

The plot 300 illustrates two of the dimensions along which the visual stimulus 116 can vary to make the visual stimulus 116 more or less difficult to see (and track). A higher spatial frequency means that the spatial details of the pattern are finer. Higher contrast means a starker difference between light and dark areas of the visual stimulus 116. Either or both of these parameters may be manipulated to find a subject's threshold—the spatial frequency above which, or the contrast below which, the stimulus can no longer be seen and/or tracked.

Figure 4:
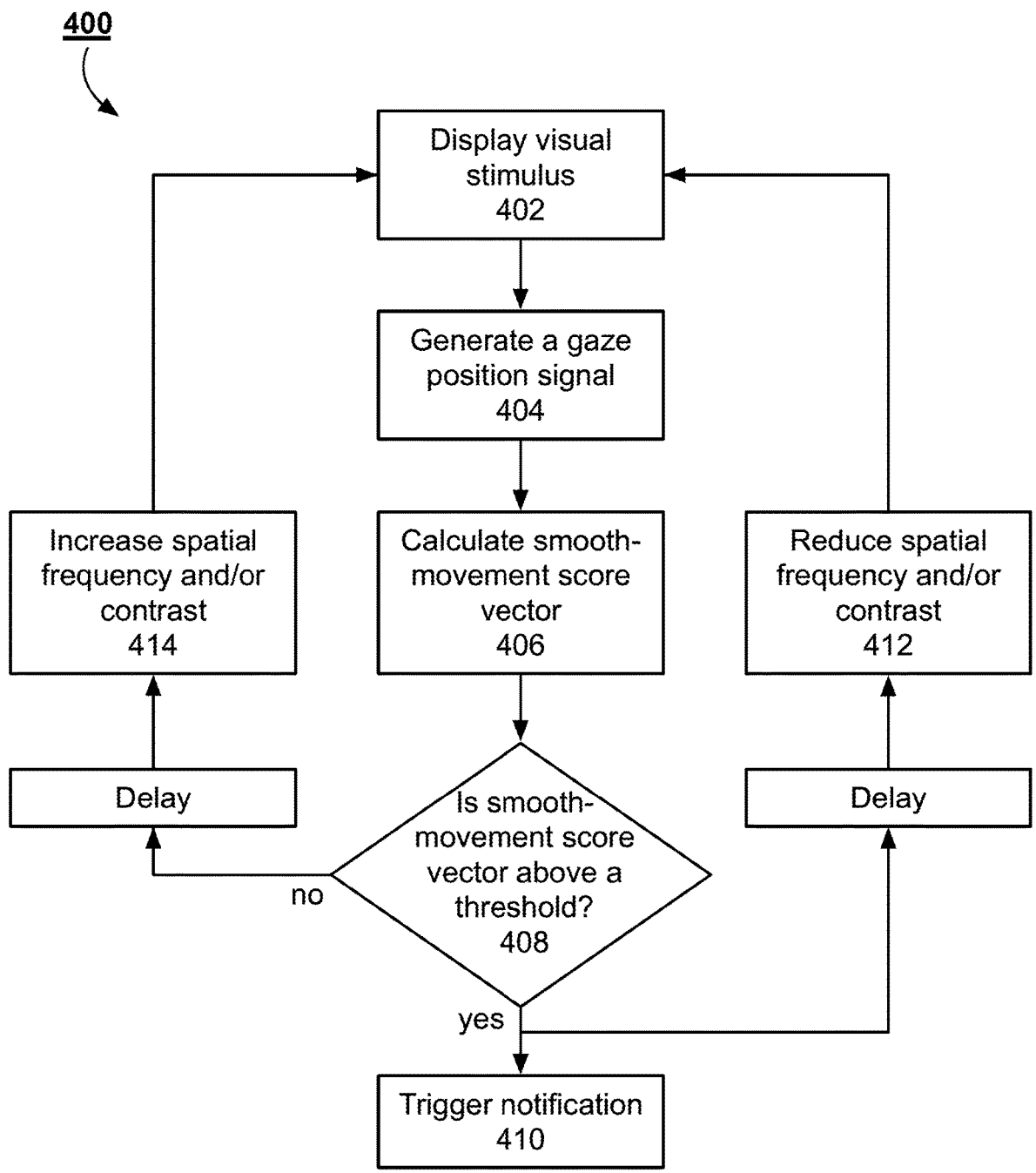
FIG. 4 illustrates a block diagram of an example method to detect smooth eye movements.

FIG. 4 illustrates a block diagram of an example method 400 to detect smooth eye movements. The method 400 includes displaying a visual stimulus (ACT 402). The method 400 includes generating a gaze position signal (ACT 404). The method 400 includes calculating a smooth-movement score vector (ACT 406). The method 400 includes determining whether the smooth-movement score vector is above a predetermined threshold (ACT 408). If the smooth-movement score vector is above a predetermined threshold, a notification is triggered (ACT 410). Also, if above the threshold, the spatial frequency and contrast can be reduced (ACT 412). If the smooth-movement score vector is below the threshold, the spatial frequency and contrast can be increased (ACT 414).

As set forth above, the method 400 can begin with the display of a visual stimulus 116 (ACT 402). The data processing system 102 can cause the visual stimulus 116 to move on a display from a first location 118 to a second location 120. The visual stimulus 116 can move to the second location 120 by scrolling across the display 122. The visual stimulus 116 can move across the screen at a speed, contrast, and spatial frequency as set by the pursuit detector 106. The pursuit detector 106 can set the speed, contrast, and spatial frequency of the stimulus by loading a test protocol.

As the visual stimulus 116 is displayed on the display 122, the system 100 can generate a gaze position signal (ACT 404). The gaze position signal can be generated by an eye-tracking monitor 112. The gaze position signal can include samples that indicate the gaze position of the eye 114 at each sample time. The gaze position signal can include signals for one, both, an average or weighted sum of the subject's eyes. The gaze position signal can include signals for a better-performing or worse-performing of the subject's two eyes at any given moment. The gaze position signal can include horizontal and vertical gaze position.

The pursuit detector 106 can calculate a smooth-movement score vector (ACT 406). The smooth-movement score vector can indicate a degree of smoothness of the detected eye movement. The smooth-movement score vector can indicate a movement relationship level between the gaze position signal and the visual stimulus 116 moving across the display 122.

The pursuit detector 106 can compare the samples of the smooth-movement score vector to a predetermined threshold (ACT 408). If the smooth-movement score vector sample is above the predetermined threshold, the pursuit detector 106 can trigger a notification (ACT 410). The notification can be a visual, auditory, or haptic notification, alone or in combination. For example, the notification can be the playing of music when the smooth-movement score vector is above the predetermined threshold. In some implementations, when the smooth-movement score vector is above the threshold, one or both of the contrast and spatial frequency of the visual stimulus 116 can be reduced and the method 400 can be repeated. The contrast and spatial frequency can be reduced to determine the limits of the subject's visual ability. The contrast and spatial frequency can be reduced after a predetermined delay (e.g., after the smooth-movement score vector remains above the threshold for the delay time) or at the end of a trial.

If the smooth-movement score vector is below the threshold, the pursuit detector 106 can increase one or both of the contrast and spatial frequency (ACT 414). The contrast and spatial frequency can be increased after a predetermined delay (e.g., after the smooth-movement score vector remains below the threshold for the delay time) or at the end of a trial.

EXAMPLES

Example 1

The systems described herein can be used as a diagnostic tool. The present system can be used to detect smooth modes of eye movement including smooth pursuit (SP), optokinetic nystagmus (OKN) and pathological nystagmus (PN), and interspersed saccadic eye movements (SEMs)

In one example, the detection and assessment of visual function can be inferred by detecting SP and/or OKN. The presence of these responses can be evidence that the visual system of the person can detect the stimulus that is driving the response. Stimulus parameters, such as the contrast and spatial frequency of the visual stimulus, can be varied to establish the limits of the person's visual capabilities. Initiation of OKN, and maintenance of both SP and OKN, are mediated by a reflex—therefore, the system enables assessment of vision even in subjects who cannot follow instructions, such as infants or people with severe brain damage.

By homing in on stimuli that are at the limit of the person's ability to see, and by giving the person repeated practice and reinforcement with those challenging stimuli, the system can be used to improve visual function in cases of cortical visual impairment caused by damage, developmental disorders or degeneration.

The system can also enable the diagnosis of neurological conditions via detection and characterization of SP, OKN, PN, and SEMs. Abnormalities in SP/OKN/SEM, and the presence of PN, may indicate stroke, head trauma, concussion, toxicity, damage to the vestibular system, or other neurological problems.

For example, the system can be used for (1) quantitative assessment of a person's ability to see, by researchers and clinicians, such as neurologists, optometrists, pediatricians and therapists. It may also be used as (2) a therapeutic tool for improving visual function in people whose vision is affected by amblyopia or other abnormalities in, or damage to, the central nervous system.

Human vision is a complicated function involving the eye and brain. The eye is both an optical device that projects visual information on the back of the eye, and a movable effector under control of the motor system that actively seeks visual stimuli and compensates for their motion. In both of these aspects it serves to maximize the usefulness of the information reaching the retina that lines the back of the eye, which detects light and processes the light into organized neural activity. The information is then sent to the brain, which further processes the activity into a visual percept. Thus, human vision can be impaired not only by refractive defects and disorders of the eye, but also by factors that originate in the brain's visual and motor systems. Cortical visual impairment (CVI) may result from damage to the brain (for example, from stroke, anoxia or traumatic brain injury) or from abnormal development.

A common type of developmental CVI is amblyopia, in which the vision in one eye is far worse than the other: the brain processes signals preferentially from the better eye, suppressing (and thereby perpetuating underdeveloped processing of) the signals from the weaker eye. Amblyopia is a widespread problem, affecting 2-4% of the population. Aside from refractive error, it is the most frequent cause of vision loss in infants and young children. It also triples the lifetime risk of subsequent serious vision loss in the better eye. It is most likely to develop if the vision in one eye is impaired by other factors (e.g. strabismus or cataract) during a critical period of child development. Its consequence is that vision deficits persist even after the triggering factor is surgically corrected. The term critical period refers to a number of overlapping periods during childhood, in which the visual system is particularly susceptible to different forms of change driven by visual experience. Though there is evidence that plastic changes in the visual cortex can still occur even during adulthood, the brain is more susceptible to plastic changes at a younger age. Hence, there is a large incentive to detect and address amblyopia and other CVIs as early as possible, both to halt the progression of impairments as they develop, and to take advantage of the brain's greater plasticity during critical periods to reverse them.

When the source of visual impairment is in the eye, it can usually be assessed by examining the eye—for example, using an autorefractor to determine the eye's refractive ability, or using an ophthalmoscope or optical coherence tomography to assess the health of the retina. By contrast, CVI is not easily viewed, so its assessment requires a behavioral response from the subject. This is relatively easy when the subject can understand and follow instructions, and can give a reliable response—for example, when they can tell the examining clinician verbally whether they can see a certain stimulus clearly, poorly or not at all. Unfortunately, many of the people who are most at risk of CVI cannot do this: they are often infants, or otherwise unable to understand or carry out instructions, perhaps due to brain damage, dementia, low IQ, or movement disorders that impair the ability to communicate a response.

The present systems and methods address the first challenge by leveraging the phenomena of optokinetic nystagmus (OKN) and smooth pursuit (SP), which are two characteristic modes of movement by which the eye "tracks" a moving visual scene to stabilize its retinal image. Both modes can include phases in which the gaze position of the eye moves (a) smoothly and (b) at a predictable velocity relative to the visual stimulus. These characteristics of eye movement may not be observed simultaneously unless stimulus information has reached key areas of the brain—thus, the presence of SP and/or OKN is positive evidence of the visual system's ability to process the stimulus. To address the second challenge, the present systems and methods can incorporate an algorithm for real-time detection of smooth eye movement, such as the algorithm described above.

Figure 5:
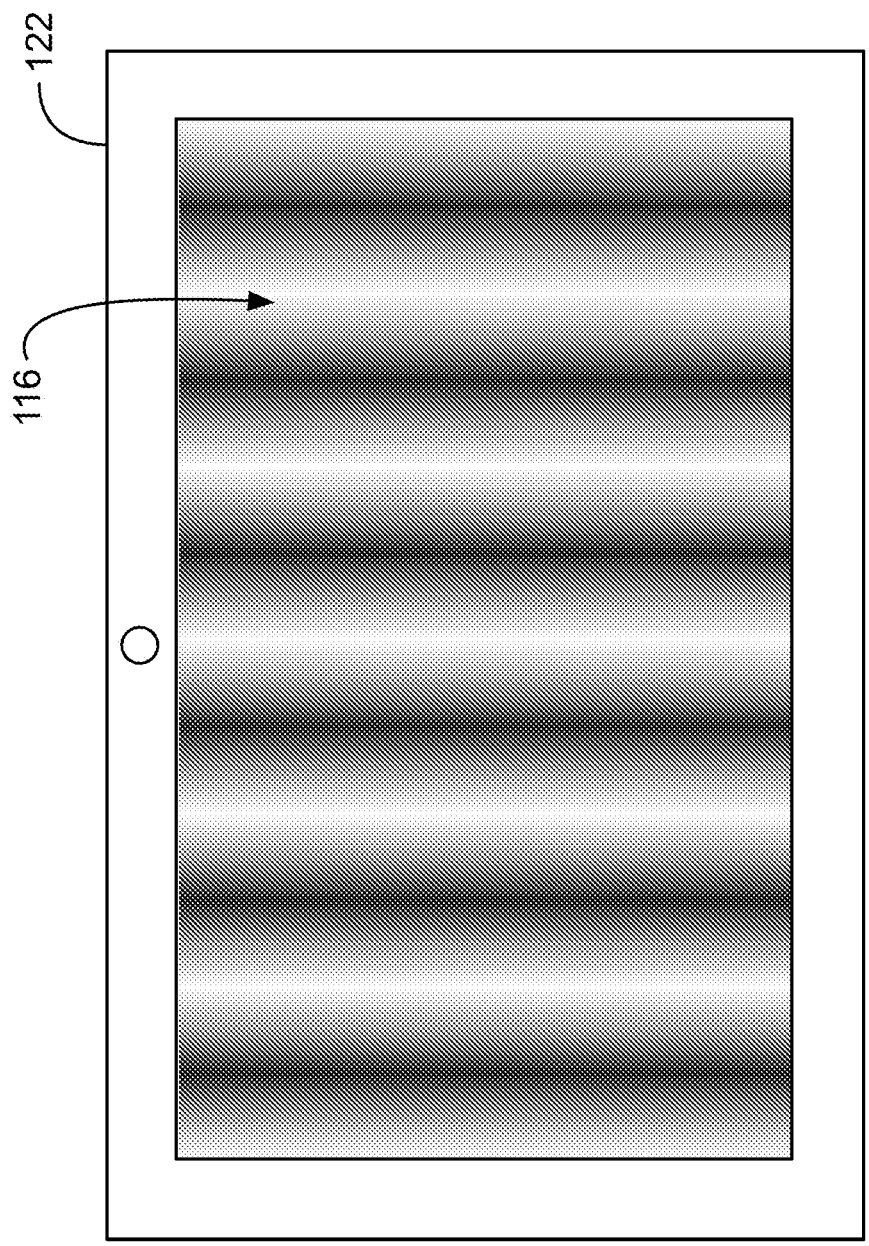
FIG. 5 illustrates an example visual stimulus for a clinical setting.

In a diagnostic setting, the system generates a visual stimulus 116 at a particular contrast and spatial frequency. For example, FIG. 5 illustrates an example visual stimulus 116. The visual stimulus 116 illustrated in FIG. 5 is a linearized, sinusoidal-modulated grating (e.g., a light and dark stripe pattern) as is the standard in much of vision science.

The system can choose a velocity (e.g., a direction and speed) for each stimulus and moves the visual stimulus 116 smoothly and continuously at this velocity.

Continuously, the pursuit detector 106 can detect whether the subject is looking in the general direction of the visual stimuli. Whenever this is not the case, the music (e.g., the notification) does not play. In clinical/scientific implementations, some other sign is also given to alert both subject and operator that the subject is not looking. In desktop implementation, for example, the pursuit detector 106 can tint the whole screen orange until the subject is positioned correctly and attending adequately. The operator has the option of attempting to attract the subject's attention by pressing a button to cause animated characters to cross the screen.

When the subject is positioned correctly and attending adequately, the pursuit detector 106 can continuously detect whether the subject's eyes are moving smoothly at a velocity close to that of the stimulus. If so, the music plays to encourage the subject to continue tracking (e.g., the notification); if not, the music is paused.

In some implementations, in "manual" mode the operator may judge whether or not the subject was able to track the visual stimulus 116, based on the amount of music that has been produced while the subject was looking at the screen in the absence of animated characters. The operator then presses a button to classify the trial as a "hit" or "miss" accordingly. In "automatic" mode, the visual stimulus 116 gathers data for a pre-configured number of seconds, and performs a statistical test described above after each such trial to answer the same hit-or-miss question. The statistical test is the same as the one used by the underlying algorithm to turn the music on or off, but instead of using a short sliding window it evaluates over the whole period of the trial. The clock that determines when a trial has elapsed, and the buffer that gathers data for evaluation, are both suspended while animated characters are visible. After a hit, the stimulus is made harder to see or to track (by decreasing contrast and/or increasing spatial frequency). After a miss, the stimulus is made easier to see or to track (by increasing contrast and/or decreasing spatial frequency). The software may be configured to stop as soon as the subject can no longer track, or a psychophysical staircase procedure may be implemented to home in more thoroughly on the subject's visual threshold.

After each measurement, the procedure is repeated with pseudo-random variation in stimulus direction and speed, allowing post-hoc analysis to verify that periods of detected smooth eye movement are not the result of pathological nystagmus.

The system can store and archive the raw data, and can be called upon later to display an analysis summary. For clinicians and scientists, this is a detailed quantitative account of the stimulus parameters that did and did not elicit tracking, and the resulting threshold.

Example 2

Figure 6:
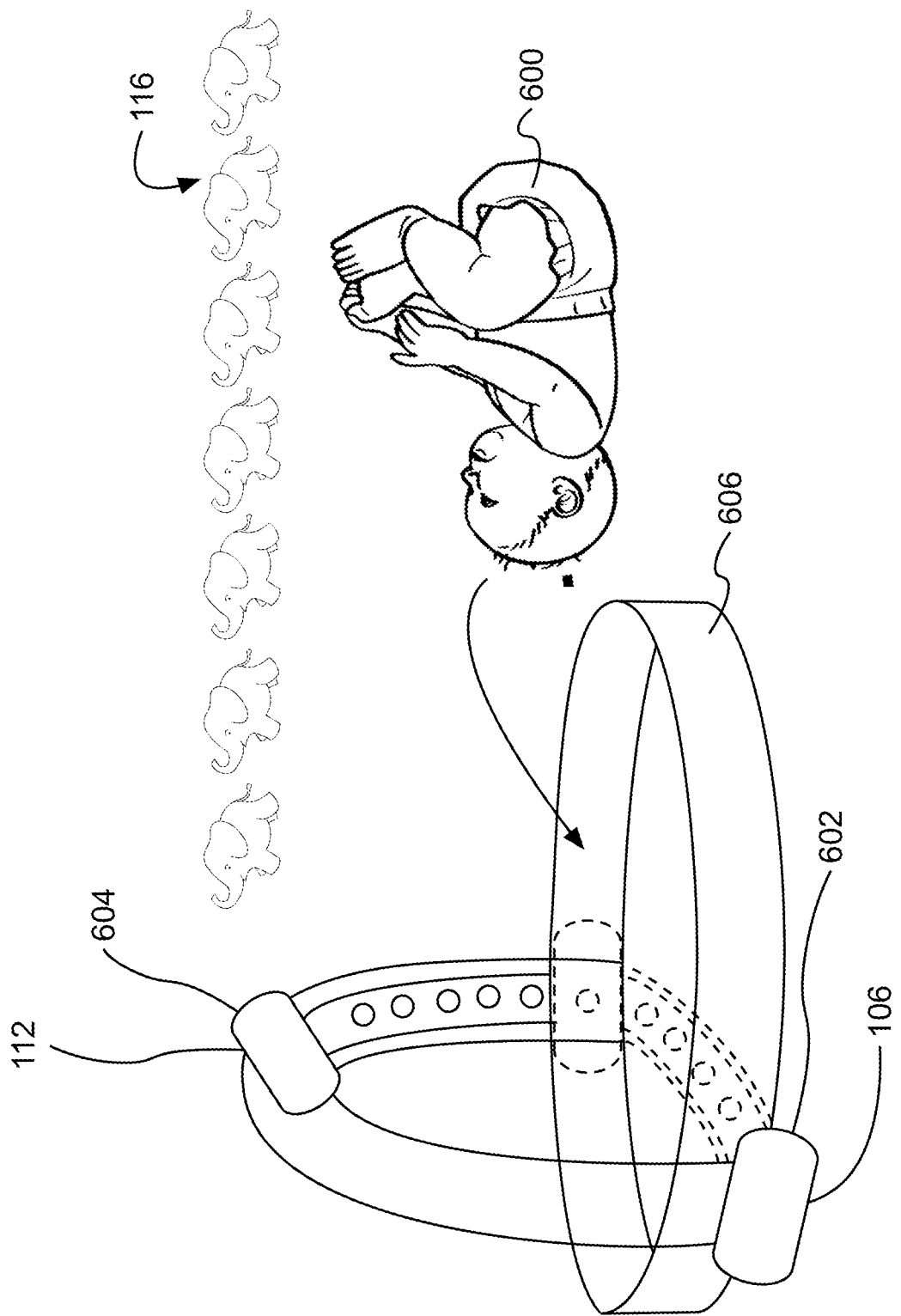
FIG. 6 illustrates another example where the system is implemented into an infant's toy.

FIG. 6 illustrates another example where the system 100 is implemented into an infant's toy. The infant 600 can be placed in a bed or bassinet 606. The system 100 can be positioned above and within the visual field of the infant 600. The system can include an eye-tracking monitor 112. A speaker 604 that plays music can be positioned near the eye-tracking monitor 112. A notification, such as music, can be played when the pursuit detector 106 detects smooth eye movements generated when the infant 600 is tracking the visual stimulus 116. In this example, the visual stimulus 116 is a continuous loop of colorful elephants. The visual stimulus 116 can be printed on a strip of white cloth or plastic that provides high contrast between the background and the visual stimulus 116. The visual stimulus 116 (e.g., the elephants) printed on the strip is a physical visual stimulus. A motor 602 can drive the strip through the infant's visual field as the eye-tracking monitor 112 detects the infant's eye gaze position.

The implementation illustrated in FIG. 6 provides an opportunity for infants to interact with their visual environment at an earlier age than would otherwise be possible. The ability to follow a visual object with one's eyes develops at around age 3 months, before a baby can effectively reach for objects to manipulate them manually. The infants' eye-tracking skills can be promoted by the use of the system. The system enables the infant to influence the sounds and movement with their gaze by tracking, and receive positive reinforcement of tracking. The system can be used to monitor as well as to promote the infant's visuomotor behavior over time.

The system can be used during critical development periods during childhood in which the visual system is particularly susceptible to different forms of change driven by visual experience. The system can enable the detection of amblyopia and other CVIs as early as possible and can halt the progression of impairments as they develop by taking advantage of the brain's greater plasticity during critical periods.

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed in connection with one imple- mentation are not intended to be excluded from a similar role in other implementations or implementations.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation or embodiment, and references to "an implementation," "some implementations," "one implementation" or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed:

1. A system comprising:
   a display screen;
   a camera capable of capturing sequential images of an eye; and
   at least one processor configured to:
      display a visual stimulus moving from a first region on the display screen to a second region on the display screen;
      acquire, via the camera, a sequence of images of an eye of a subject viewing the display screen;
      determine, from the sequence of images acquired using the camera, a gaze positon signal corresponding to respective gaze positions of the eye in the sequence of images;
      compute a velocity vector from the gaze position signal;
      determine a stimulus-correlated gaze velocity estimate based on the velocity vector and a speed at which the visual stimulus moves from the first region to the second region;
      calculate, based on the stimulus-correlated gaze velocity estimate, a smooth-movement score vector indicative of a movement relationship level between the gaze position signal and the visual stimulus moving from the first region to the second region; and
      generate, responsive to the smooth-movement score vector being above a predetermined threshold, a notification as feedback while the visual stimulus is moved on the display screen.

2. The system of claim 1, wherein the gaze position signal is a horizontal gaze position signal indicating a horizontal gaze position of the eye.

3. The system of claim 1, the at least one processor configured to change a spatial frequency of the visual stimulus.

4. The system of claim 1, the at least one processor configured to change a contrast of the visual stimulus.

5. The system of claim 1, wherein the notification comprises an audible notification.

6. The system of claim 1, the at least one processor configured to display a second visual stimulus from the first region to the second region, the second visual stimulus having a spatial frequency or a contrast different than the visual stimulus.

7. The system of claim 1, wherein:
   the display screen comprises a motor; and
   the at least one processor is further configured to drive the motor at a predetermined speed to move the visual stimulus from the first region to the second region.

8. The system of claim 1, wherein the visual stimulus is a physical visual stimulus.

9. A system comprising:
   a display screen;
   an eye-tracking monitor comprising a camera capable of capturing sequential images of an eye, and configured to (i) detect a gaze position of the eye in sequential images and (ii) generate a gaze position signal corresponding to the detected gaze position, wherein the gaze position signal comprises a plurality of samples; and at least one processor configured to:
display a visual stimulus moving from a first region on the display screen to a second region on the display screen;
receive, from the eye-tracking monitor, the gaze position signal corresponding to gaze position detected as the visual stimulus moves from the first region to the second region on the display screen;
generate a count of the plurality of samples in each of a plurality of predetermined target velocity ranges;
calculate a smooth-movement score vector based on the count of the plurality of samples in each of the predetermined target velocity ranges, the smooth-movement score vector indicative of a movement relationship level between the gaze position signal and the visual stimulus moving from the first region to the second region; and
generate, responsive to the smooth-movement score vector being above a predetermined threshold, a notification as feedback while the visual stimulus is moved on the display screen.

10. A method implemented by a computer comprising at least one processor, the method comprising:
displaying, on a display screen, a visual stimulus moving from a first region on the display screen to a second region on the display screen;
generating, via an eye-tracking monitor comprising a camera capable of capturing sequential images of an eye, a gaze position signal corresponding to a gaze position of the eye detected in sequential images as the visual stimulus moves from the first region to the second region;
computing a velocity vector from the gaze position signal;
determining a stimulus-correlated gaze velocity estimate based on the velocity vector and a speed the visual stimulus moves from the first region to the second region;
calculating, based on the stimulus-correlated gaze velocity estimate, a smooth-movement score vector indicative of a movement relationship level between the gaze position signal and the visual stimulus moving from the first region to the second region; and
generating, responsive to the smooth-movement score vector being above a predetermined threshold, a notification as feedback while the visual stimulus is moved on the display screen.

11. The method of claim 10, wherein the gaze position signal is a horizontal gaze position signal indicating a horizontal gaze position of the eye.

12. The method of claim 10, further comprising changing a spatial frequency of the visual stimulus.

13. The method of claim 10, further comprising changing a contrast of the visual stimulus.

14. The method of claim 10, further comprising generating an audible notification.

15. The method of claim 10, further comprising displaying a second visual stimulus from the first region to the second region, the second visual stimulus having a spatial frequency or a contrast different than the visual stimulus.

16. The method of claim 10, further comprising driving a motor of the display screen at a predetermined speed to move the visual stimulus from the first region to the second region.

17. The method of claim 10, wherein the visual stimulus is a physical visual stimulus.

18. A method implemented by a computer comprising at least one processor, the method comprising:
displaying, on a display screen, a visual stimulus moving from a first region on the display screen to a second region on the display screen;
generating, via an eye-tracking monitor comprising a camera capable of capturing sequential images of an eye, a gaze position signal corresponding to a gaze position of the eye detected in sequential images as the visual stimulus moves from the first region to the second region, the gaze position signal comprising a plurality of samples;
generating, from the gaze position signal, a count of the plurality of samples in each of a plurality of predetermined target velocity ranges;
calculating a smooth-movement score vector based on the count of the plurality of samples in each of the predetermined target velocity ranges, the smooth-movement score vector indicative of a movement relationship level between the gaze position signal and the visual stimulus moving from the first region to the second region; and
generating, responsive to the smooth-movement score vector being above a predetermined threshold, a notification as feedback while the visual stimulus is moved on the display screen.

* * * * *